United States Patent [19]

Kist et al.

[11] Patent Number: 5,462,063
[45] Date of Patent: Oct. 31, 1995

[54] CELL COLLECTING DEVICE

[75] Inventors: Joost Kist, Amsterdam; Willem P. G. Rovers, Oss, both of Netherlands; Dirk A. Vanden Berghe, Laarne, Belgium

[73] Assignee: Futura Nova B.V., Amsterdam, Netherlands

[21] Appl. No.: 200,412

[22] Filed: Feb. 23, 1994

[30] Foreign Application Priority Data

Feb. 25, 1993 [NL] Netherlands ............................ 9300354

[51] Int. Cl.$^6$ .................................................. A61B 10/00
[52] U.S. Cl. ........................................... 128/756; 128/757
[58] Field of Search ..................... 128/749, 756, 128/757, 759; 604/1

[56] References Cited

U.S. PATENT DOCUMENTS

| | | | |
|---|---|---|---|
| 2,250,112 | 7/1941 | Larson | 15/159 |
| 2,317,485 | 4/1943 | Rider | 15/167 |
| 2,514,665 | 7/1950 | Myller | 128/2 |
| 2,739,585 | 3/1956 | Ayre | 128/2 |
| 2,767,703 | 10/1956 | Nieburgs | 128/2 |
| 2,847,990 | 8/1958 | Ayre . | |
| 3,128,488 | 4/1964 | Schad | 15/187 |
| 3,540,432 | 11/1970 | Ayer | 128/2 |
| 3,554,185 | 1/1971 | Kohl | 128/2 |
| 3,774,590 | 11/1973 | McDonald | 128/2 B |
| 3,776,219 | 12/1973 | Brown | 128/2 |
| 3,800,781 | 4/1974 | Zalucki | 128/2 |
| 3,881,464 | 5/1975 | Levere | 128/756 |
| 4,059,404 | 11/1977 | Schuster et al. | 23/230 |
| 4,127,113 | 11/1978 | Nollan | 128/2 |
| 4,311,140 | 1/1982 | Bridgman | 128/276 |
| 4,381,325 | 4/1983 | Masuda | 428/91 |
| 4,448,205 | 5/1984 | Stenkvist | 128/749 |
| 4,662,381 | 5/1987 | Inaba | 128/756 |
| 4,700,713 | 10/1987 | Kist | 128/756 |
| 4,759,376 | 7/1988 | Stormby | 128/756 |
| 5,191,899 | 3/1993 | Strickland et al. | 128/759 |

FOREIGN PATENT DOCUMENTS 2103054 7/1971 France .

OTHER PUBLICATIONS

Anderson et al, *The Cytologic Diagnosis of Endometrial Adenocarcinoma*, Am. J. Obstet. Gynecol., 125:376–383 (1976).
Ayre, *A New Diagnostic Procedure for Cancer of the Larynx Using a Retractable Throat Brush*, J.A.M.A., 156:770–141 (1954).
Ayre, *Rotating Endometrial Brush: New Technic for the Diagnosis of Fundal Carcinoma*, Obs. & Gyn., 5:137–141 (1955).
Ayre and Oren, *A New Rapid Method for Stomach–Cancer Diagnosis: The Gastric Brush*, Cancer, 6:117–1181 (1953).
Bajardi, *Material Obtained by Ceryical Scraping Only*, Acta Cytologica, 4:242 (1960).

(List continued on next page.)

*Primary Examiner*—Max Hindenburg
*Attorney, Agent, or Firm*—Wolf, Greenfield & Sacks

[57] ABSTRACT

A universally applicable cell collecting device is provided. The device has a handle and a brush head formed of flexible bristles. The bristles can be positioned such that the cross-sectional dimensions of the brush head are substantially equal in all directions. The bristles can include central bristles surrounded completely by outer bristles that are shorter and thinner than the central bristles. The bristles also can be arranged in a pattern of concentric circles and also can be arranged so that the proximal ends are spaced from one another in a predetermined array with the distal ends contacting one another in a predetermined array. The brush head also can have an outermost row of bristles having an outwardly facing surface with a radius of curvature that matches the radius of curvature of the shape of the brush head. The brush head also can be constructed and arranged such that the bristles have a resting position and a flexed position, wherein all scraping edges of the bristles are unexposed in the resting position but are exposed in the flexed position.

22 Claims, 1 Drawing Sheet

OTHER PUBLICATIONS

Ferenczy et al, *Outpatient Endometrial Sampling With Endocyte: Comparative Study of Its Effectiveness With Endometrial Biopsy*, Obs. & Gyn., 63:295–302 (1984). (Oct. 19, 1989).

Fluhmann, *The Squamocolumnare Transitional Zone of the Cervix Uteri*, Obs. & Gyn. 14:133–148 (1959).

Kriseman, *Description of a New Disposable Uterine Sampler (the Accurette) for Enmdometrial Cytology and Histology*, Sa Mediese Tydskrif, p. 107 (Jan. 23, 1982)(Jul. 23, 1990).

Richart, *Evaluation of the True Fals Negative Rate in Cytology*, Am. J. Obst. & Gynec., pp. 723–726 (Jul. 15, 1964).

Rubio, *False Negatives in Cervical Cytology: Can They be Avoided*, Acta Cytologica, 25:199–202 (1981).

Swingler, et al, *Diagnostic Accuracy of the Mimark Endometrial Cell Sampler in 101 Patients with Postmenopausal Bleeding*, British Journal of Obs & Gyn, 86:816–818 (1979).

Wachtel et al, *An Improved Sampling Device for Cervial Cytology*, The Lancet, p. 26, (Jul. 6, 1974).

M. Boon et al., *Consequences of the Introduction of Combined Spatula & Cytobrush Sampling for Cervical Cytology*, ACTA Cytologica 30(3):264–270 (1986).

Boon et al., *Analysis of Five Sampling Methods for the Preparation of Cervical Smears*, AACTA Cyctologica 33(6):843–848 (1989).

Vooijs, *Endocervical Brush Device*, Lancet, p. 784, Apr. 8, 1989.

Laverty et al., *The Importance of the Cell Sample in Cervical Cytology: A Controlled Trial of a New Sampling Device*, Med. J. Aust. 150:432–436 (1989).

Weitzman et al., *Endocervical Brush Cytology: An Alternative to endocervical Curettage*, J. Repro. Med. 33(8):677–683 (1988).

Bergeron et al., *Screening Devices of Cervical and Endometrial Ca* Contemp Ob/Gyn 28 (special issue):55–66 (1987).

NCI Workshop, *The 1988 Bethesda System for Reporting Cervical/Vaginal Cytological Diagnoses*, JAMA 262(7):931–934 (1989).

Waddell et al., *The Cervex: An Ectocervical Brush Sampler*, Cytopathology 1:171–181 (1990).

Vooijs, G. P., *Significance of Cellular Composition of Smears for The Reliability of Cytological Diagnosis*, New Frontiers in Cytology pp. 413–420.

Macgregor, *Wat Constitutes an Adequate Cervical Smear*, Br. J. Ob/Gyn 98:6–7 (1991).

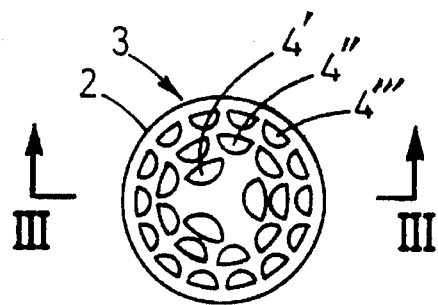
Fig.2
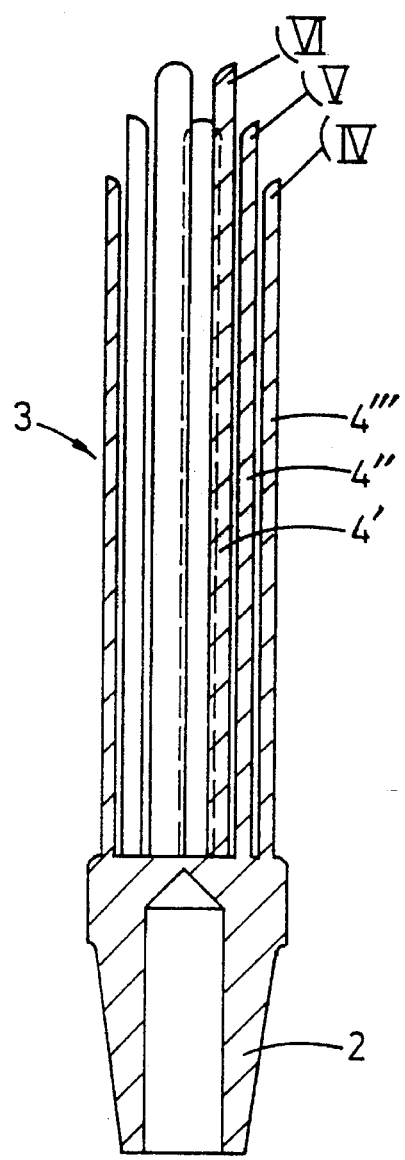
Fig.3
Fig.4
Fig.5
Fig.6
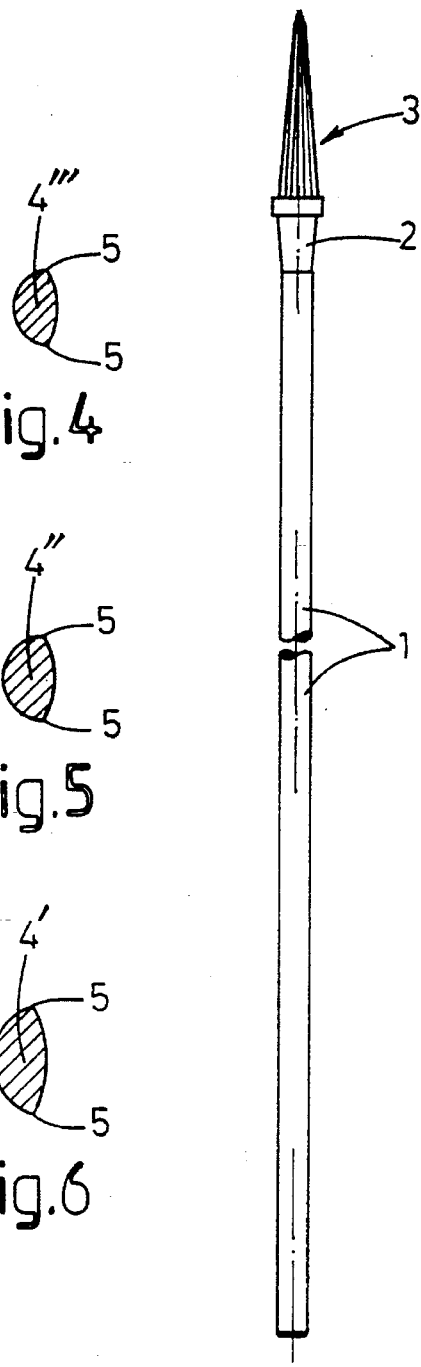
Fig.1

CELL COLLECTING DEVICE

FIELD OF THE INVENTION

The present invention relates to cell collecting devices and more particularly to a universally applicable cell collecting device adapted for safe and efficient collection of cells from the human body.

BACKGROUND DESCRIPTION

In the medicinal and biological fields, cells, body fluids and microorganisms are commonly collected from humans and other living creatures for subsequent study. Typically, cells are removed from a body cavity with an instrument and thereafter retained for further examination. Such cells may be placed on a slide for microscopic examination, on a culture medium for microbiological culture studies, or in a receptacle for preserving such cells during transport to a laboratory. Procedures are routinely performed to remove and study cells from such body cavities as the nasal, throat, anal, vaginal, cervical, and urethral cavities as well as from surgical wounds and topical skin sites.

With such cell collection procedures, safety is a great concern. In particular, it is desirable to collect the specimen from a body cavity without irritating the site or causing trauma. Additionally, it is desirable to avoid causing infection at the collection site.

One prior art cell collection instrument includes a stick or handle made of wood, plastic or metal which carries a cotton tip on a distal end thereof. During use, the distal end of the instrument is inserted into a body cavity and the cotton tip is brushed against the wall of the cavity for collecting cells therefrom. The cotton tip retains the cells which are thereafter released for subsequent study.

This prior art cell collection instrument has the disadvantage that humid cells (i.e., wet cells or cells collected in a humid environment) are absorbed within the cotton tip and are not easily released therefrom. Additionally, the cotton tip or a portion thereof, in certain instances, remains at the cell collection site within the body cavity causing sometimes harmful bodily reactions such as inflammation. In certain circumstances, the remaining tip portion can only be removed surgically.

Other prior art cell collection devices include plastic bristles. One such prior art cell collection instrument, particularly suited for cell collection from the cervix, is described in U.S. Pat. No. 4,700,713 to Kist. The device of Kist includes a longitudinal stem or handle having a carrier at a distal end thereof and a head including a plurality of parallel flexible bristles attached to the carrier and extending longitudinally and distally from the carrier. Each bristle has a longitudinally extending sharp edge. During use the head is inserted through the uterus opening into the cervix. The handle is then rotated, causing the sharp edges of the bristles to scrape against the cervix wall and collect cells therefrom.

A disadvantage of the Kist device is that the shape and outer dimension of the head of bristles prevents use of the device with body cavities other than the cervix. Additionally, and also due to the shape and outer dimension of the head, the bristles may contact the cervix wall during insertion and removal, potentially causing irritation or trauma.

Accordingly, the general object of the present invention is to provide an improved device for collecting cells or other biological materials, which both safely and efficiently collects samples from a site on or within the human body.

SUMMARY OF THE INVENTION

The devices of the invention all include a handle having a proximal end and a distal end. The handle preferably defines a longitudinal axis. A plurality of flexible bristles are attached to the distal end of the handle, preferably extending substantially parallel to the axis, and define a brush head. Each bristle can include one or more longitudinal scraping edges.

According to one aspect of the invention, the bristles are positioned such that the cross-sectional dimensions of the brush head are substantially equal in all dimensions.

According to another aspect of the invention, the bristles include central bristles surrounded completely by outer bristles that are shorter and thinner than the central bristles.

According to another aspect of the invention, the bristles are constructed and arranged in a pattern of concentric circles.

According to another aspect of the invention, each bristle has a proximal end and a distal end. The proximal ends are attached to the handle and are spaced from one another in a predetermined array. The distal ends also are positioned in a predetermined array. The distal ends can be positioned closer to one another than are the proximal ends, and in one preferred embodiment the distal ends contact one another in the predetermined array.

According to another aspect of the invention, the bristles include an outermost row that defines an overall shape of the brush head, the shape having a radius of curvature. The bristles of the outermost row have an outwardly facing surface with a radius of curvature that matches the radius of curvature of the shape of the brush head.

According to still another aspect of the invention, the bristles have a resting position and a flexed position, and each bristle has at least one longitudinal scraping edge. The scraping edges are unexposed in the resting position and at least some of the scraping edges are exposed in the flexed position. Thus, when the device is rotated along its longitudinal axis and the bristles are in the unflexed position, only a smooth surface such as a cylinder or a cone contacts the tissue, the smooth surface being defined by the smooth outwardly facing surfaces of the bristles. In this manner, the device may be inserted into the body cavity, presenting only a smooth surface. Thereafter, the device may be rotated, and the resistance of the tissue or the pressure or torsion applied by the user flexes the bristles out of the smooth, predetermined arrangement and orients the bristles for scraping. Tissue then is scraped as the device is rotated.

According to still another aspect of the invention, the bristles may be provided with only two sides, a first rounded side and a second rounded side. The sides meet to form scraping edges. The first rounded side has a first radius of curvature and the second rounded side has a second radius of curvature that differs from the radius of curvature of the first rounded side. Preferably the outwardly facing surface has the larger radius of curvature.

In still other preferred embodiments, the cross-section of at least a part of the bristles can include a larger dimension and a smaller dimension, with the larger dimension oriented in a circumferential direction with respect to the brush head. And in others, the bristles can include two scraping edges, positioned on tangential sides of the bristles in relation to the rotational axis of the device.

The brushes of the invention can include one or many of the features described above. The preferred embodiment, described in detail below, includes most of the foregoing features. It further is characterized by a carrier which is formed integrally with the bristles, the carrier in turn being attached to the handle. The carrier is substantially round in cross-section and has bristles uniformly distributed over it in a circumferential direction. The preferred device further has a brush head that is free of bristles along the center of the carrier along the longitudinal axis. As will be seen, the bristles are symmetrically oriented in relation to the longitudinal axis.

BRIEF DESCRIPTION OF THE DRAWINGS

The foregoing and other objects and advantages of the invention will become more clear after a reading of the following detailed description of the preferred embodiments and brief description of the drawings in which:

FIG. 1 is a side view of a preferred embodiment of the cell collecting device according to the present invention FIG. 2 is a cross-sectional view of a brush head, illustrating the outlay of the bristles on the carrier;

FIG. 3 is a cross-sectional view of the brush head of FIG. 2, taken along lines III—III showing further details of the arrangement of the bristles on the carrier; and FIGS. 4, 5 and 6 are cross-sectional views of an inner, mid, and outer bristle shown respectively in FIG. 3, but drawn in an enlarged scale.

DETAILED DESCRIPTION

The preferred embodiment includes parallel bristles together forming a brush head, one end of the bristles being fixed on a carrier. The bristles are positioned such that the cross dimensions of the brush head is substantially equal in all directions. By using plastic bristles, wet or humid cells are not absorbed so that they can easily be delivered again in order to be examined. Furthermore, the shape of the brush head makes the device suitable for various uses, both in cavities and on the body surface. Of course a circular outer circumference of the carrier and brush offers the best possibilities for universal application, but it is also conceivable that said shapes are slightly adapted for different purposes and consequently also include oval, square or similar shapes.

As mentioned above, the scraping action of the bristles is only activated if the brush is deformed. For example, when cells are collected from a cavity the bristles will be inactive upon insertion and removal and only when the brush head is rotated, the torsion of the bristles will cause their scraping edges to be oriented outwardly thereby being able to scrape cells from the wall. Upon removal of the brush head from the body cavity, the bristles will move back to the inactive position, thereby positioning the collected cells removed from the outwardly facing surface of the brush head. In this way, it is prevented that cells or other biological material collected on the scraping edges are given back to the wall of the cavity. In this manner, great and representative amounts of cells, body fluids or micro-organisms may therefore be gathered. The scraping edges of the bristles may also be activated by pushing the free end of the brush head against the end of the body cavity causing the brush to bulge outwardly and thereby permitting the scraping edges of the bristles to become effective. Also the deformation against a flat surface can make the scraping edges active. In relation to the term scraping edges, it is noted that these edges need not be completely sharp but preferably may be slightly rounded. One therefore may also speak of scraping edges with bristles having an elliptical or oval-shaped cross-section.

To further reduce the risk of trauma upon insertion and removal of the brush head of the device into and out of a body cavity, it may be an advantage when the bristles positioned on the circumference of the brush head are of such cross-section that they form a substantially smooth cylinder-shaped outer circumference of the brush head. This can be realized, for example, in that the circumference of the bristles is defined by two circular segments having different radius of curvature and joining each other at an acute angle. In this case, the radius of curvature of the circular segment of each hair, which is positioned on the circumference of the brush head will correspond to or match the radius of curvature of the whole brush head.

The preferred embodiment includes fourteen bristles 4''' in the outermost row, nine bristles 4'' in the middle row and three bristles 4' in the innermost row. The outwardly facing surfaces of the outermost bristles 4''' define a radius about the central axis of the brush head of 3.0 mm. The outwardly facing surfaces of the middle row of bristles 4'' define a radius of 2.25 mm, and the innermost row of bristles 4' have outwardly facing surfaces defining a radius of 1.5 millimeters. The bristles 4''' of the outermost row have a width of 0.5 mm and have an inwardly facing surface defining a radius of 0.5 mm. These bristles are 23.5 mm long. The bristles 4'' of the middle row are 0.5 mm in width and have an inwardly facing surface defining a radius of 0.5 mm. The length of the bristles 4'' is 25.5 mm. The bristles 4' of the innermost row have a width of 0.7 mm and an inwardly facing surface defining the radius of 0.75 mm. The length of the bristles 4' are 27.5 mm.

A very advantageous embodiment of the device according to the invention is characterized in that the outer circumference of the brush head defined by the bristles is conical from the carrier toward the free end. In this manner, the introduction of the brush head into a body cavity is facilitated on one hand, while also the introduction of the brush head into a receptacle containing transport medium is simplified, or the diameter of the transport medium receptacle may be decreased causing the volume of the receptacle to be reduced leading to a saving of transport medium, on the other hand.

The drawing shows exemplary embodiments of a device for scraping and collecting body cells, and body fluids and for collecting intra and extra cellular micro-organisms.

As shown in FIG. 1, the device includes an elongate straight plastic handle 1 on the one end of which a carrier 2 having a brush head 3 is removably attached. The brush head 3 includes in this embodiment a plurality of bristles 4 extending substantially parallel to the longitudinal axis of the handle 1 and being fixed on one end to the carrier 2 with a uniform distribution. The carrier 2 and the bristles 4 are integral and made of plastic, such as for instance polyethylene Exxon LDPE 653, by injection moulding. Of course also other materials and other production techniques may be used.

As shown in FIG. 1, at least the bristles positioned at the circumference of the brush head 3 extend from the carrier 2 conically or tapered so that the brush head 3 has the form of a tapered cone having a smooth outer wall.

For the sake of simplicity FIG. 2 and 3 show the bristles 4 parallel to each other, but in practice the bristles will extend in accordance with FIG. 1.

Referring to FIG. 2, the bristles are arranged in three circular rows around the center of the carrier 2, the bristles 4' being the thickest ones and the bristles 4" and 4''' in the rows toward the outer circumference are progressively thinner. This is clearly shown in FIGS. 4–6. The number of bristles in a circular row increase towards the outer circumference. The cross-section of the bristles consist of two circular segments having a larger and smaller radius of curvature, wherein both circular segments join each other at an angle of approximately 90 degrees, defining a more or less sharp edge indicated as scraping edge 5 (Fig. 4–6). The radius of curvature of the circular segment at the outer circumference of the respective row of bristles 4', 4", 4''', and in particular at the outer circumference of the brush head 3, corresponds to the radius of curvature of the brush head 3 in its entirety. This is clearly shown in FIG. 2. The cross-section of the bristles 4 is equal along the full length, but it would of course also be conceivable that the bristles taper towards their free end. The centrally positioned bristles 4' are not only thicker but also longer than the bristles 4''' positioned outwardly thereof and the bristles 4''' in turn positioned outwardly of these. This makes it possible that the brush head 3 tapers to a point on the free end, which facilitates the introduction into cavities. Since the bristles 4' near the center of the carrier 2 are thicker than those outwardly thereof, these bristles 4' effect a rigidification in the center of the brush head 3.

When the device has collected cells, body fluids or intra and extra cellular micro-organisms, these may selectively be directly smeared onto a slide for microscopic examination and on culture medium for microbiological cultures, or be put into a receptacle containing preserving or transport medium in order to be transported to a laboratory. Then the handle 1 is separated from the carrier 2 and brush head 3.

The device according to the invention as described above and shown in the drawing offers many advantages. First of all, large amounts of cells are collected (typical endocervical cell in endocervical samplings). The device may also be introduced into all kinds of body openings so that the device according to the invention may replace the usual cotton bud in nose and throat sampling, in anal, vaginal and cervical samplings and for microbial isolation with skin diseases. Samples may also be taken from surgical wounds or the like. Based thereon, the device according to the invention is applicable both in the microbiology, cytopathology and in PCR technology, so that one can actually speak of a universally applicable cell collecting device.

The invention is not restricted to the embodiment shown in the drawing and described above, which may be varied in different manners within the scope of the invention. The bristles of the brush head may for instance be formed on the carrier in all kinds of other arrangements. For example, the bristles may be arranged symmetrically, as seen in circumferential direction of the carrier, and may also be suited for a rotation of the device in one direction, this in contrast to the embodiment shown which is operational in opposite rotational directions. Also the cross-section of the bristles may be varied and may include for example rectangular, square or other polygonal shapes, and also round, oval or other shapes and mixtures thereof are conceivable with or without the formation of one or more scraping edges. The term "bristle" is used herein to indicated that the cell collecting means are elongate and elastically bendable and together form a bristle or pencil-shaped head. The flexibility of the bristles will generally be such that a deformation is possible without excessive forces, but the brush head will have a certain rigidity in longitudinal direction in order to assist in a proper introduction into body cavities.

We claim:

1. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, the bristles being positioned such that the cross-sectional dimensions of the brush head are substantially round.

2. A device as claimed in claim 1, wherein the bristles include central bristles completely surrounded by outer bristles that are thinner and shorter than the central bristles.

3. A device as claimed in claim 1 wherein each bristle includes 2 scraping edges positioned on tangential sides of the bristles in relation to the rotational axis of the device.

4. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, the bristles including central bristles surrounded completely by outer bristles that are shorter and thinner than the central bristles.

5. A device as claimed in claim 4, wherein each bristle has a proximal end and a distal end, the proximal ends being attached to the handle, and wherein the proximal ends are spaced from one another in a predetermined array.

6. A device as claimed in claim 5, wherein the distal ends are spaced from one another in a predetermined array and are spaced more closely to one another than are the proximal ends.

7. A device as claimed in claim 5, wherein the distal ends contact one another in a predetermined array.

8. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, wherein the bristles are arranged in a pattern of concentric circles.

9. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, wherein each bristle has a proximal end and a distal end, wherein the proximal ends are attached to the handle and are spaced from one another in a predetermined array, and wherein the distal ends contact one another in a predetermined array.

10. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, wherein the bristles include an outermost row that defines an overall shape of the brush head, the shape having a radius of curvature, and wherein the bristles of the outermost row have an outwardly facing surface with a radius of curvature that matches the radius of curvature of the shape of the brush head.

11. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, wherein the bristles have a resting position and a flexed position, wherein each bristle has at least one longitudinal scraping edge, and wherein all scraping edges are unexposed in the resting position and wherein at least some scraping edges are exposed in the flexed position.

12. A device for collecting cells or other biological materials for examination thereof, comprising a handle having a proximal end and a distal end and defining a longitudinal axis, and a plurality of flexible bristles attached to the distal end of the handle, extending substantially parallel to the axis and defining a brush head, wherein each bristle has only two sides, a first rounded side and a second rounded side, wherein the sides meet to form scraping edges, and wherein the first rounded side has a first radius of curvature and the second rounded side has a second radius of curvature that differs from the radius of curvature of the first rounded side.

13. A device as claimed in claim 1, 4, 9, 10, 11 or 12, wherein the bristles are arranged in a pattern of concentric circles.

14. A device as claimed in claim 1, 4, 8, 9 or 10, wherein the bristles have a resting position and a flexed position, wherein each bristle has at least one longitudinal scraping edge, and wherein all scraping edges are unexposed in the resting position and wherein at least some scraping edges are exposed in the flexed position.

15. A device as claimed in claim 12, wherein the bristles have a resting position and a flexed position, and wherein all scraping edges are unexposed in the resting position and wherein at least some scraping edges are exposed in the flexed position.

16. A device as claimed in claim 1, 4, 8, 10, 11 or 12, wherein the brush head is conical from the proximal ends of the bristles to the distal ends of the bristles.

17. A device as claimed in claim 1, 4, 8, 9 or 10, wherein each bristle has at least one longitudinal scraping edge.

18. A device as claimed in claim 4, 8, 9, 10 or 11, wherein each bristle includes two scraping edges positioned on tangential sides of the bristles in relation to the rotational axis of the device.

19. A device as claimed in claim 12 wherein the scraping edges of each bristle are positioned on tangential sides of the bristles in relation to the rotational axis of the device.

20. A device as claimed in claim 4, 8, 9, 10, 11 or 13, wherein the cross-section of at least a part of the bristles includes a larger dimension and a smaller dimension, and wherein the larger dimension of each bristle is oriented in a circumferential direction with respect to the brush head.

21. A device as claimed in claim 4, 8, 9, 10, 11 or 12, wherein the bristles are positioned such that the cross-sectional dimensions of the brush head are substantially equal in all directions.

22. A device as claimed in claim 8, 9, 10, 11 or 12, wherein the bristles include central bristles surrounded completely by outer bristles that are shorter and thinner than the central bristles.

* * * * *